United States Patent
Kitaori et al.

(10) Patent No.: US 7,887,679 B2
(45) Date of Patent: Feb. 15, 2011

(54) METHOD OF STERILIZATION AND ELECTROLYTIC WATER EJECTING APPARATUS

(75) Inventors: Noriyuki Kitaori, Hachioji (JP); Masaharu Uno, Fujisawa (JP); Yoshinori Nishiki, Fujisawa (JP); Tsuneto Furuta, Fujisawa (JP)

(73) Assignees: Permelec Electrode Ltd., Kanagawa (JP); Institute of National Colleges of Technology, Japan, Tokyo (JP)

( * ) Notice: Subject to any disclaimer, the term of this patent is extended or adjusted under 35 U.S.C. 154(b) by 1280 days.

(21) Appl. No.: 11/452,937

(22) Filed: Jun. 15, 2006

(65) Prior Publication Data
US 2007/0023273 A1  Feb. 1, 2007

(30) Foreign Application Priority Data
Jun. 16, 2005 (JP) ............... P.2005-176801

(51) Int. Cl.
*C25B 9/08* (2006.01)
*C25B 1/13* (2006.01)
(52) U.S. Cl. ............... 204/260; 205/626
(58) Field of Classification Search .......... 204/260; 205/626
See application file for complete search history.

(56) References Cited

U.S. PATENT DOCUMENTS

| | | | | | |
|---|---|---|---|---|---|
| 3,282,825 | A | * | 11/1966 | Brown et al. | 204/520 |
| 4,260,468 | A | * | 4/1981 | Bradley | 204/260 |
| 2003/0062267 | A1 | | 4/2003 | Nakamura et al. | |
| 2004/0213698 | A1 | | 10/2004 | Tennakoon et al. | |

FOREIGN PATENT DOCUMENTS

| | | | |
|---|---|---|---|
| JP | 9-268395 A | | 10/1997 |
| JP | 2000-197889 A | | 7/2000 |
| JP | 2003-266073 A | | 9/2003 |
| JP | 2004-129954 A | | 4/2004 |
| WO | 02/48054 A1 | | 6/2002 |
| WO | WO 0248054 A1 | * | 6/2002 |

OTHER PUBLICATIONS

Extended European Search Report dated Jun. 6, 2008.
European Office Action dated May 28, 2009.

* cited by examiner

*Primary Examiner*—Alexa D. Neckel
*Assistant Examiner*—Nicholas A. Smith
(74) *Attorney, Agent, or Firm*—Sughrue Mion, PLLC (57) ABSTRACT

The present invention provides a method of sterilization with an electrolytic water, including: electrolyzing a raw water with an electrolytic unit including: a cathode; and an anode at least having a part containing a conductive diamond to prepare an electrolytic water; and ejecting the electrolytic water to a substance to be sterilized, and an electrolytic water ejecting apparatus.

3 Claims, 2 Drawing Sheets

METHOD OF STERILIZATION AND ELECTROLYTIC WATER EJECTING APPARATUS

FIELD OF THE INVENTION

The present invention relates to a method of sterilization with electrolytic water containing, dissolved therein in a high concentration, a product of electrolysis such as ozone, which is used for sterilization, cleaning, bleaching, etc. The invention further relates to an ejection apparatus which ejects the electrolytic water.

BACKGROUND OF THE INVENTION

Common bacteria widely inhabit soils, rivers, lakes and marshes, etc. in the natural world. Consequently, there has been more interest in techniques being capable of sterilizing such common bacteria or making such common bacteria bacteriostatic without fail as well as being safe for the human body. Chlorine bactericides such as sodium hypochlorite, calcium hypochlorite, and sodium dichloroisocyanurate have been extensively used as bactericides/disinfectants in a wide range of environments. However, the use of such chlorine bactericides in large quantities have come to arouse troubles. For example, in factories and retail stores where food materials are handled in large amounts, cleaning with a sodium hypochlorite solution having a concentration exceeding 100 ppm is being conducted and this not only spoils the flavors of the food materials but also causes a problem that the sterilizing enhances danger (increase in trihalomethane (THM)).

It has recently become known that electrolytic water yielded by electrolysis is useful in the fields of agriculture, foods, etc. Attention is being directed to the excellent sterilizing/disinfectant activity of electrolytic water, and investigations are being made on the use of the water in clinical activities and in the home. Examples of the uses thereof which are being investigated include the sterilization/disinfection of diseased parts, incised parts, percutaneous openings for stationary catheters, etc. and the sterilization/disinfection of domestic utensils or articles, such as kitchen utensils, baby articles, and furniture, and house equipments, such as the toilet facilities and bathtub.

There are the following three kinds of electrolytic water which have been permitted as food additives.

(1) Weakly alkaline electrolytic hypo-water (additive name: electrolytic sodium hypochlorite water; 20-200 ppm; pH>7.5; electrolytically yielded from 0.2-2% aqueous sodium chloride solution using no diaphragm)

(2) Slightly acid electrolytic water (additive name: slightly acid hypochlorous acid water; 10-30 ppm; pH=5-6.5; electrolytically yielded from 2-6% hydrochloric acid using no diaphragm)

(3) Strongly acid electrolytic water (additive name: strongly acid hypochlorous acid water; 20-60 ppm; pH<2.7; yielded as anolyte water from 0.2% aqueous sodium chloride solution in a diaphragm type cell)

The acid waters among those kinds of electrolytic water have the following merits.

(1) The acid waters are superior in safety because THMs are less apt to generate under acid conditions.

(2) Resistant bacteria are less apt to generate and on-site management is easy.

(3) The waters can be used for treatment in combination with the alkaline electrolytic water.

(4) The waters can be utilized like tap water and impart no odor to the hands or fingers.

(5) Use of the waters just before suffices (sterilization time is short).

In the conventional treatment with sodium hypochlorite solutions, use of this chemical having a concentration up to 200 ppm as a food additive has been permitted. However, the addition thereof spoils the flavor and the chemical is apt to remain. In contrast, the electrolytic water has a high sterilizing effect even in a low concentration and is beneficial, although use thereof necessitates an initial investment in the production apparatus.

Such electrolytic water is obtained by electrolyzing water (raw water to be electrolyzed) to which a solute generating ions upon dissolution, e.g., sodium chloride, has been added, optionally together with an acid for pH adjustment. The electrolysis is conducted using either an electrolytic cell having an electrode pair consisting of an anode and a cathode or an electrolytic cell having a constitution comprising an anode, a cathode, and a diaphragm disposed between them.

Such an apparatus for electrolytic-water production is of a large scale and it is difficult to use it for more easily conducting sterilization/disinfection or the like in clinical activities or in the home. Under these circumstances, portable small electrolytic-water spray apparatus have been proposed (see references 1 to 3 given below).

[Reference 1] JP-A-2000-79393
[Reference 2] JP-A-2000-197889
[Reference 3] JP-A-2001-276826

Besides those, known techniques include JP-A-2004-129954 (an apparatus having a device generating the power necessary for electrolysis), JP-A-2004-130263 (the proportion of the inner volume of a piston to the volume, sectional area, etc. of a cell cylinder part is specified), JP-A-2004-130264 (raw water to be electrolyzed comprising a pH adjuster, surfactant, chlorine compound, and water is used to obtain electrolytic water having a pH of 3-8.5), JP-A-2004-130265 (the electrolytic water disclosed in JP-A-2004-130264 is used in a foamed state), JP-A-2004-130266 (the direction of voltage application to the electrodes is switched alternately), JP-A-2004-148108 (the voltage to be applied to the electrodes is made changeable), JP-A-2004-148109 (electrodes are disposed in a suction passage), JP-A-2003-93479, JP-A-2003-266073, JP-A-2002-346564 (separation type having a cylindrical electrode in a spray part), and JP-A-2001-47048 (gun type designed to be prevented from clogging in non-ejection periods; equipped with a motor).

However, the long-term use of hypochlorites for sterilization has yielded bacteria resistant to hypochlorite chemicals. The sterilizing effects of these chemicals have hence become insufficient and there is a doubt about the effectiveness thereof.

On the other hand, ozone-containing water has been placed on food additive lists and has gained approval of FDA (Food and Drug Administrations) of U.S.A. (2001) for use as a bactericide in food storage/production steps. Ozone-containing water has already come into many practical uses for sterilization in food factories and the sterilization of foods themselves. Recently, attention is focused on the fact that ozone-containing water is equal or superior in effect to sterilizing waters heretofore in use also in clinical fields such as dermatology, ophthalmology, and dentistry and is effective in reducing the burden to be imposed on the living body.

Ozone-containing water has the following two merits.

(1) The sterilizing effect of ozone (OH radical) is based on the oxidative destruction of cell walls and this indiscriminate activity is thought not to generate resistant bacteria.

(2) Ozone does not have residual tendency.

When ozone-containing water is used in combination with an oxidizing agent having residual tendency (e.g., a hypochlorite, persulfate, or percarbonate) according to need, a more effective sterilization treatment is possible.

Consequently, use of ozone-containing water can be one measure in eliminating the problem described above. However, there are drawbacks that the production of ozone-containing water necessitates a large apparatus and ozone-containing water does not last long. It has hence been difficult to spread ozone-containing water to general homes.

Conventional Process for Producing Ozone-Containing Water

Ozone-containing water has conventionally been produced generally with a discharge type ozone gas generator. Ozone-containing water having a concentration of several ppm can be easily produced by the process, and is being utilized in the fields of water purification treatment and food cleaning. However, the apparatus has been unsuitable for use as a handy ozonized-water production apparatus having excellent instant-response characteristics and yielding high-concentration ozone-containing water, for the following reasons.

(1) The ozonized-water production necessitates two steps, i.e., first generating ozone as a gas and then dissolving the gas in water.

(2) The ozone-containing water has a lower concentration than that produced by the electrolytic process described below and, hence, the water should be produced through high-pressure injection into water and dissolution therein.

(3) The power source for ozone generation has a high voltage and a high frequency, making it difficult to attain a size reduction.

(4) In the ozonized-water production apparatus based on a discharge, a certain time period (stand-by time of several minutes) is required for the ozone gas generation ability to become stable and it is difficult to instantaneously prepare ozone-containing water having a certain concentration.

Electrolytic Ozone Production Process

In contrast, the electrolytic process readily yields high-concentration ozone gas and ozone-containing water although inferior to the discharge process in electric power consumption rate. The electrolytic process is in general use in special fields such as, e.g., the cleaning of electronic parts. Since a direct-current low-voltage power source is employed because of the principle of the process, the apparatus is excellent in instant-response characteristics and safety and is expected to be used as a small ozone gas generator or a small ozonized-water production apparatus. According to applications, a driving mode can be selected from battery driving, power-generator driving, and AC-DC conversion driving.

For efficiency generating ozone gas, it is indispensable to select a proper catalyst and electrolyte. A noble metal such as platinum, α-lead dioxide, β-lead dioxide, or glassy carbon impregnated with a fluorocarbon has been used as an electrode material, while an aqueous solution of sulfuric acid, phosphoric acid, or a fluorine-group-containing solute has been used as an electrolyte. However, these materials have poor handleability and the spread thereof is slow.

On the other hand, a water electrolysis cell which employs a solid polymer electrolyte as a diaphragm and in which pure water is used as a feed material is easy to handle and manage and is in general use [J. Electrochem. Soc., 132, 367 (1985)]. Even in this water electrolysis cell, ozone gas having a concentration as high as 12% or above is obtained when lead dioxide, which has been employed as a catalyst, is used. However, lead dioxide is exceedingly unstable and it is necessary to apply a protective current for maintaining the electrolytic performances and current efficiency.

In the system called a direct electrolysis system, the solution located around an electrode is caused to flow at a sufficient rate and taken out as ozone-containing water (JP-A-8-134677). However, since the catalyst usable therein is limited to a stable one such as, e.g., a noble metal, so as to prevent the catalyst from fouling the water, this system has been low in current efficiency and concentration. The system has further had a problem that there is a phenomenon in which the electrode activity decreases upon standing. Although a measure can be taken to avoid the phenomenon by always applying a backup protective current, this makes the apparatus complicated to constitute an obstacle to a size reduction.

Furthermore, in the case where raw water other than pure water is supplied to the electrolysis system, the activity of the noble-metal electrode catalyst itself is influenced by the quality of the water. Care should hence be given to the fact that electrolytic performances such as life and efficiency fluctuate.

Known Techniques Concerning Diamond Electrodes and Electrolytic Water/Electrolytic Treatment Journal of Electrochemical Society, Vol. 141, 3382-, (1994) reported the stability of diamond in an acid electrolytic solution, while U.S. Pat. No. 5,399,247 discloses that an organic wastewater can be decomposed using diamond as an anode material.

JP-A-1997-268395 discloses that diamond is useful as an electrode for producing functional water (containing ozone). JP-A-2000-254650 discloses a water treatment with an oxidizing agent and an aqueous hydrogen peroxide solution produced with a diamond anode. JP-A-2001-192874 discloses that a diamond electrode is useful as an electrode for synthesizing persulfuric acid.

Furthermore, JP-A-2004-211182 discloses that a diamond electrode is useful as an electrode for synthesizing percarbonic acid. JP-A-2005-046730 discloses electrolytic sterilization with electrolytic water containing oxy acid ions.

SUMMARY OF THE INVENTION

As described above, it is known to use electrolytic water for the sterilization of a substance to be sterilized, etc. However, the ozone-containing water, which is one of the electrolytic water, is unstable and difficult to store. It is hence preferred to synthesize the ozone-containing water just before use in the case of using the ozone-containing water. However, no ozonized-water producing apparatus which is small and stable has been developed so far because of the various problems attributable to an ozone generator as described above. Although on-site type apparatus for producing various kinds of electrolytic water including ozone-containing water, which has sterilizing/bleaching ability, have been proposed, all these apparatus yield electrolytic water which has a low concentration of ozone, etc., and does not have a satisfactory sterilizing or bacteriostatic function. None of these has been put to practical use.

An object of the invention is to provide an electrolytic water ejecting apparatus which eliminates the problems of the related-art techniques described above and which electrolytically produces an electrolytic species, e.g., ozone, in a high concentration to enable a sterilizing or bacteriostatic treatment of a substance to be conducted on a satisfactory level.

The present inventors have made eager investigation to examine the problem. As a result, it has been found that the foregoing objects can be achieved by the following method of sterilization and electrolytic water ejecting apparatus. With these findings, the present invention is accomplished.

The present invention is mainly directed to the following items:

1. A method of sterilization with an electrolytic water, comprising: electrolyzing a raw water with an electrolytic unit comprising: a cathode; and an anode at least having a part containing a conductive diamond to prepare an electrolytic water; and ejecting the electrolytic water to a substance to be sterilized.

2. The method of sterilization according to item 1, wherein the raw water is a pure water, and the electrolytic water is an ozone-containing water.

3. The method of sterilization according to item 2, wherein an ozone concentration of the ozone-containing water is 0.1 ppm or higher.

4. The method of sterilization according to item 1, wherein the electrolytic unit further comprises a voltage changing device to control a voltage to be applied so as to control the amount of the electrolytic water to be prepared.

5. The method of sterilization according to item 1, wherein the raw water contains at least one of a pH adjuster and a surfactant.

6. An electrolytic water ejecting apparatus comprising: a vessel containing a raw water; an electrolytic unit comprising: a cathode; and an anode at least having a part containing a conductive diamond; and a head to eject an electrolytic water prepared by electrolyzing the raw water with the electrolytic unit.

7. An electrolytic water ejecting apparatus according to item 6, which further comprising a sheet-form diaphragm member, wherein the anode has a shape of a rod and the cathode has a shape of a wire, and the sheet-form diaphragm member is disposed around the anode and the cathode is disposed around the sheet-form diaphragm member.

The invention will be explained below in detail.

In the method of the invention, an anode at least having a part including a conductive diamond is used to yield electrolytic water. In the invention, the electrolytic water is preferably an ozone-containing water, which is yielded by applying a voltage to an electrolytic unit. By the use of this conductive-diamond electrode, an active species such as, e.g., ozone is efficiently synthesized in a high concentration, whereby electrolytic water having sterilizing/bleaching ability can be easily produced.

The method and electrolytic water ejecting apparatus of the invention can be extensively used in applications such as the domestic or business-purpose deodorization, sterilization, or bleaching of the interior of a room, water-related facilities, tableware, clothes, etc. or the sterilization or disinfection of human body parts, e.g., the hands or fingers. As apparent from the above explanation, the term "sterilization" in the method of sterilization of the invention includes deodorization, bleaching, disinfection, and the like besides sterilization.

Typical anode reactions in the electrolytic unit are shown below as overall schemes.

Water reacts according to schemes (1) and (2) to yield oxygen and ozone.

$$2H_2O = O_2 + 4H^+ + 4e \quad (1)$$

$$3H_2O = O_3 + 6H^+ + 6e \quad (2)$$

When a chloride ion is present, it reacts according to scheme (3) to yield hypochlorous acid.

$$Cl^- + H_2O = ClO^- + 2H^+ + 2e \quad (3)$$

When sulfuric acid has been added, it reacts according to scheme (4) to yield persulfuric acid.

$$2SO_4^{2-} = S_2O_8^{2-} + 2e \quad (4)$$

When a carbonic acid ion is present, it reacts according to scheme (5) to yield percarbonic acid.

$$2CO_3^{2-} = C_2O_6^{2-} + 2e \quad (5)$$

Use of conductive diamond in place of a conventionally used electrode material enables the reactions shown by schemes (1) to (5) to readily proceed, whereby those peroxides are electrolytically produced extremely efficiently. Besides those electrolytically yielded species, OH radicals and oxidized forms of the electrolyte generate at the diamond electrode. The sterilizing/bleaching effects of these radicals and oxidized forms and those of the electrolytically yielded species shown above can be synergistically utilized.

The electrolytic water thus produced, which contains electrolytically yielded species in a high concentration, is ejected from the apparatus to a substance to be sterilized. Preferably, the electrolytic water is sprayed in an atomized state on the substance. It is desirable that the production and ejection of the electrolytic water be continuously conducted. For example, a switch engaged with a trigger is operated to apply a voltage to the electrolytic unit to produce electrolytic water containing electrolytically yielded species in a high concentration and, simultaneously with or just after the production, the electrolytic water is ejected to or sprayed on a substance to be sterilized. As a result, the substance to be sterilized is sterilized with the high-concentration species yielded electrolytically, whereby the purpose is accomplished.

Besides the acid water which has been permitted as a food additive, electrolytic water containing two or more electrolytically yielded species, such as, e.g., oxygen, ozone, hypochlorous acid, and peroxides, can be efficiently produced according to the invention by suitably selecting conditions, e.g., an electrolyte.

Furthermore, a novel sterilizing/detergent effect can be produced by adding an organic acid/surfactant for pH adjustment for the purpose of improving sterilizing ability or by adding an alcohol or the like for the purpose of, e.g., improving sterilizing ability or refreshing feeling.

On the other hand, in the case where electrolysis is conducted using pure water as raw water, ozone-containing water only is mainly produced and sprayed. This case has an advantage that the spraying leaves no residues such as a salt.

The invention further has the following features.

(1) Although lead oxide or a platinum catalyst is unstable and indispensably necessitates a backup, the electrolytic water ejecting apparatus of the invention, which employs conductive diamond as an anode material, has improved electrode durability.

(2) The electrolytic water ejecting apparatus of the invention is safe, small, and lightweight; these features are impossible to the apparatus for producing ozone-containing water through a discharge.

(3) The electrolytic water ejecting apparatus of the invention has excellent instant-response characteristics. Namely, the electrolytic production of electrolytic water and the ejection or spraying of the electrolytic water can be conducted substantially simultaneously. The apparatus for producing ozone-containing water through a discharge has no instant-response characteristics because ozone gas is generated by a discharge and this gas is dissolved in water to produce ozone-containing water.

(4) A driving source can be selected in a wide range including battery driving, power-generator driving, and AC power source driving (adapter), and a switch can be linked with the trigger.

(5) Highly active electrolytic water such as the following ones can be produced according to the conditions used.

(a) Alkaline electrolytic water (electrolytic water containing two or more peroxides depending on electrolyte selection; sulfates, carbonates, etc., besides chlorides)

(b) Acid electrolytic water (electrolytic water containing two or more peroxides depending on electrolyte selection; sulfates, carbonates, etc., besides chlorides)

(c) High-concentration ozone-containing water (having no residual tendency, having sterilizing activity at least 10 times the sterilizing activity of hypochlorous acid systems, and further having bleaching effect; the ozone half-value period is prolonged depending on coexistent substances, resulting in improved effect retention)

(d) Novel composite electrolytic water (novel sterilizing effect is produced by adding an organic acid/surfactant for pH adjustment for the purpose of improving sterilizing ability or by adding an alcohol or the like for the purpose of, e.g., improving sterilizing ability or refreshing feeling)

The electrolytic water ejecting apparatus of the invention is most suitable for use as a small electrolytic-water spray. However, because the apparatus has the features specifically shown above, the apparatus is not limited to small ones for domestic use. The apparatus can be made to be usable in fields where continuous mass-production is required, such as food factories, agriculture, and medical activities, by increasing the scale of the apparatus based on the techniques described above.

According to the invention, due to the use of conductive diamond as at least part of the anode material, electrolytic water containing electrolytically yielded species, such as ozone and peroxides, dissolved therein in a high concentration can be electrolytically produced highly efficiently. By ejecting or spraying this electrolytic water on a substance to be sterilized, the substance can be sterilized with the high-concentration species yielded electrolytically.

The reference numerals used in the drawings denote the followings, respectively.

1, 21 electrolytic-water spray apparatus
2 raw water
3 vessel
4 head
5, 22 transport tube
6, 28 electrolytic unit
7, 24, 24' anode
8, 27 diaphragm
9, 26 cathode
12 spray nozzle
13 trigger arm
17 trigger-engaged switch

DETAILED DESCRIPTION OF THE INVENTION

The components of the electrolytic water ejecting apparatus of the invention will be explained below. However, the constitutions of the components in the invention should not be construed as being limited to the following.

Anode

The electrolytic unit in the invention comprises an anode and a cathode and optionally includes a diaphragm.

Of these components, the anode is one in which the anode material is wholly or partly constituted of conductive diamond. This anode material is deposited on an anode substrate to produce the anode. In the invention, an electrode at least having a part containing the conductive diamond may be simply referred to as a "diamond electrode".

Diamond is excellent in thermal conductivity, optical transparency, and resistance to high temperatures and oxidation, and the electrical conductivity thereof can be regulated especially by doping. Diamond is hence regarded as a promising material for use in semiconductor devices and energy conversion elements. Diamond electrodes are inert in water decomposition reaction. It has been reported that a diamond electrode in electrolytic oxidation yields ozone and hydrogen peroxide besides oxygen, as described in documents cited above.

The presence of a conductive diamond as part of the anode suffices, and the substrate may be partly exposed.

The substrate is not limited to silicon (monocrystalline or polycrystalline), and usable examples thereof include niobium, tantalum, zirconium, titanium, molybdenum, tungsten, graphite, and various carbides. A suitable material can be selected according to applications. An electrode material can be deposited on the surface of such a substrate having any desired shape heretofore in general use, such as a mesh, pipe, rod, or beads.

An explanation is given below on the production of the anode by the hot-filament CVD method, which is a typical process for diamond production.

An organic material serving as a carbon source, such as a hydrocarbon, e.g., methane $CH_4$, or an alcohol, is introduced into a CVD chamber together with hydrogen gas. While the atmosphere in the chamber is kept being a reducing atmosphere, the filament is heated to heat the atmosphere to a temperature at which carbon radicals generate, i.e., 1,800-2,400° C. An electrode substrate is set in an area having a temperature (750-950° C.) at which diamond deposition occurs. The concentration of the hydrocarbon gas is preferably 0.1-10 vol % based on the hydrogen, and the pressure is preferably from 20-1,013 hPa (1 atm).

For imparting satisfactory conductivity to the diamond, it is needed to add a slight amount of an element differing in valence, e.g., boron (B) or phosphorus (P). The content of the element is preferably 10-10,000 ppm, more preferably 100-3,000 ppm.

Trimethylboron [$(CH_3)_3B$] can be used as a boron source compound. Also usable is boron oxide $B_2O_3$, which is less toxic. Usable examples of phosphorus source compounds include diphosphorus pentoxide $P_2O_5$.

Cathode

Cathode reactions include hydrogen evolution as the main reaction. It is therefore preferred to use an electrode catalyst which is not embrittled by hydrogen. Examples of such preferred electrode catalysts include platinum group metals, nickel, stainless steel, titanium, zirconium, gold, silver, and carbon. The cathode substrate is limited to materials such as stainless steel, zirconium, carbon, nickel, titanium, and diamond. In the electrolytic water ejecting apparatus of the invention, it is preferred to use a material having excellent oxidation resistance because the cathode is disposed so as to be in contact with water containing ozone and peroxides dissolved therein.

Diaphragm

In order that the active substances generated by electrode reactions might be prevented from coming into contact with the counter electrode and kept stable, it is preferred to interpose a neutral diaphragm or an ion-exchange membrane ingredient between the electrodes.

The diaphragm may be either of a fluororesin membrane and a hydrocarbon resin membrane. However, the former membrane is preferred from the standpoint of resistance to corrosion by ozone and peroxides. The ion-exchange membrane not only serves to prevent substances generated at the anode or cathode from being consumed at the counter electrode as stated above, but also functions to enable the electrolysis to proceed speedily even when the liquid has a low conductivity. Use of an ion-exchange membrane is hence effective when a feed material having poor conductivity, such as, e.g., pure water, is used.

Shapes of Electrodes/Diaphragm

It is preferred that the electrolytic unit be housed in a suction/transport passage for raw water (transport tube) constituted of a tube.

The shapes of the two electrodes and diaphragm and the relative positions thereof are not particularly limited as long as the production of electrolytic water is not adversely influenced.

It is preferable that the anode has a shape of a rod (hereinafter simply referred to as "rod anode"). Furthermore, it is preferable that the diaphragm is a sheet-form diaphragm member, and the sheet-form diaphragm is disposed around the anode. Besides, it is preferable that the cathode is a wire cathode disposed around the sheet-form diaphragm member. In the case where a rod anode is used, an ion-exchange membrane in a strip form having a width of 1-10 mm is preferably used in order to secure a water flow. It is preferred to spirally wind this ion-exchange membrane around the rod anode so that the gap between adjacent strip edges is kept at 1-10 mm. In this case, the wire cathode is employed and is disposed so as to be in contact with that side of the strip diaphragm which is opposite to the anode.

The electrodes may have a flat shape. In the case of using a diaphragm, however, the electrodes preferably have openings for passing raw water therethrough. Grooves or perforations may be formed in this case. In the case where the electrodes are parallel plates, it is preferred to employ a porous diaphragm for the purposes of removing gas components evolved and supplying an electrolytic solution component as a feed material.

A solid porous material having ion-exchange ability (solid polymer electrolyte) may be packed in the space between the electrodes. Examples of the porous material include commercial ion-exchange resin particles, and such resins include hydrocarbon resins such as styrene resins, acrylic acid resins, and aromatic polymers. However, ion-exchange particles made of a fluororesin are preferred from the standpoint of corrosion resistance. It is also possible to deposit an ingredient having ion-exchange ability on an appropriate porous support member. Furthermore, a fibrous material in the form of a web is also convenient. The porosity of the porous material is preferably 20-90% from the standpoints of even dispersion of the liquid and resistivity. The size of the pores or material particles is preferably 0.1-10 mm.

Electrolysis Conditions

The electrolysis temperature and the current density are preferably 0-60° C. and 0.01-1 A/cm$^2$, respectively, from the standpoint of the stability of the peroxides yielded. The electrode spacing should be as small as possible so as to reduce resistance loss. However, the electrode spacing is preferably regulated to 0.1-5 mm in order to attain a reduced pressure loss in water supply and maintain an even flow distribution.

The material of the raw-water transport tube, which has the electrolytic unit disposed therein and will be described later, preferably is a hydrocarbon resin such as PP, PVC, or PE, a fluororesin, or the like. In the case where a tank for storing raw water therein is disposed, the material of the tank is one selected from materials having resistance to raw water.

The electrolytic unit of the invention preferably has a voltage changing device to control a voltage to be applied so as to control the amount of the electrolytic water to be yielded.

Raw Water and Electrolytic Water Produced

There is no particular need of dissolving an electrolyte in the raw water in the invention. For obtaining pure ozone-containing water, a feed material such as distilled water or ion-exchanged water can be used and supplied to the electrolytic unit having an ion-exchange resin ingredient.

In the case where the solution (raw water) to be contained in the vessel is pure water, the quality of this pure water preferably is on the level attained with ordinary ion-exchange resins. Specifically, the quality thereof is preferably 0.1 MΩcm or higher, especially preferably 1 MΩcm or higher, in terms of conductivity. Besides pure water, an electrolyte solution can be used for yielding hypochlorous acid and peroxides. Examples of such salts include one or more members selected from sodium chloride, potassium chloride, magnesium chloride, calcium chloride, ammonium chloride, sodium sulfate, sodium carbonate, hydrochloric acid, sulfuric acid, sodium hydroxide, ammonia, and the like. The salt concentration in the raw water preferably is 0.1-10% by weight.

The composition and concentration of the electrolytic water to be produced can be regulated according to the intended use. In the case where the electrolytic water is intended to be used for food treatment, it should be produced as the alkaline electrolytic hypochlorite water, slightly acid electrolytic water, or ozone-containing water permitted by the Ministry of Health and Welfare. In the case where the electrolytic water is intended to be used for sterilization/bleaching, an electrolyte may be selected so as to yield a peroxide suitable for the substance to be treated. It is desirable that the electrolytic water obtained has an ozone concentration of 0.1 ppm or more, more preferably 0.1-100 ppm. Besides, it is also desirable that the electrolytic water obtained has a hypochlorous acid concentration of 1-1,000 ppm, persulfuric acid concentration of 1-1,000 ppm, and/or percarbonic acid concentration of 1-1,000 ppm. When the concentrations of these active species are lower than the lower limits, there are cases where no sterilizing effect is brought about.

In the invention, the raw water preferably further contains at least one of a pH adjuster and a surfactant for reasons below.

Regarding the pH adjuster, detailed explanations are described below. In the case where hypochlorous acid is to be yielded by electrolyzing raw water, use of an acid solution as the raw water results in the presence of a larger amount of hypochlorous acid than a hypochlorite, while use of an alkaline solution results in the presence of a larger amount of a hypochlorite than hypochlorous acid. Sterilizing ability varies depending on the nature of the solution. In general, acid solutions often have higher sterilizing ability than alkaline solutions. In the control of, in particular, spores and the like, acid solutions have higher sterilizing activity than alkaline solutions. In contrast, with respect to sterilizing activity against mold, alkaline solutions are more active than acid solutions. It is therefore preferred that the nature of the solution should be suitably regulated so as to be acid or alkaline according to the substance to be treated through ejection or spraying to thereby impart improved sterilizing activity thereto.

In case where the solution is regulated so as to be acid by adding a strong acid to the solution to excessively enhance acidity, the hypochlorous acid suffers decomposition to generate chlorine gas and, as a result, the oxidizing ability which brings about the sterilizing ability of hypochlorous acid is impaired. For enhancing sterilizing ability while maintaining the oxidizing ability of the hypochlorous acid, it is preferred to regulate the solution so as to have a pH of 3-7 at 20° C. For regulating the solution so as to have such a pH, it is preferred to use a pH adjuster. Examples of the pH adjuster include a water-soluble organic weak acid having a low degree of dissociation from the standpoint of ease of pH adjustment. Examples of the water-soluble organic acid include succinic acid, lactic acid, acetic acid, citric acid, and tartaric acid.

Besides, for regulating the solution so as to be alkaline, it is preferred to add sodium carbonate, sodium hydrogen carbonate, ammonium carbonate, or the like. Such carbonates are oxidized to percarbonic acid through electrolysis.

Regarding the surfactant, detailed explanations are described below. A surfactant may be added to the solution in order to further improve sterilizing ability. Addition of a surfactant to the solution not only improves the ability of the solution after electrolysis to wet the substance to be treated therewith through ejection or spraying, but also improves the affinity of the solution for the cell membranes of mold and germs. Thus, the sterilizing effect is further improved.

Usable examples of the surfactant include anionic surfactants such as alkylbenzenesulfonic acid salts and polyoxyethylene alkyl ether sulfuric acid salts, cationic surfactants such as benzalkonium chlorides, amphoteric surfactants such as amine oxides (e.g., alkyldimethylamine oxides), and nonionic surfactants such as polyglycerol fatty acid esters and alkylglycosides. The concentration of the surfactant in the solution is preferably 0.01-10% by weight.

Besides those ingredients, an alcohol may be added to the solution for the purpose of, e.g., improving sterilizing ability and refreshing feeling. Furthermore, additives such as, e.g., a perfume, colorant, bactericide other than surfactants, thickener, enzyme, bleaching agent, chelating agent, electrolyte other than chlorine compounds, rust preventive, builder, and antiseptic such as ethanol or a paraben may be added according to need. It is especially preferred from the standpoint of storage stability that the electrolytic water contain an antiseptic.

It is known that by dissolving carbonic acid, acetic acid, ethanol, or the like beforehand in the water, the efficiency of ozone utilization and ozone stability are improved. This is because the solubility of ozone in these ingredients is higher than in water and, hence, ozone gas can be effectively utilized as ozone-containing water, or because those ingredients serve to trap OH radicals, which accelerate ozone decomposition, and thereby stabilize the ozone-containing water. It is therefore preferred to dissolve any of those substances in raw water in an appropriate amount beforehand.

When raw water containing metal ions in a large amount, such as tap water, well water, or seawater, is used, there is a possibility that hydroxides or carbides might deposit on the surface of the cathode to inhibit reactions. Furthermore, oxides such as silica deposit on the anode surface. For eliminating this problem, a reverse current is preferably caused to flow at an appropriate time interval (from 1 minute to 1 hour), whereby ingredients are acidified at the cathode and alkalified at the anode. As a result, gas evolution and feed water fluidization occur to accelerate the reactions. Thus, reactions for removing the deposits readily proceed.

The apparatus may be one in which a device for reversing the direction of voltage application to the electrodes has been united therewith, or may be one which has the device disposed separately therefrom.

When tap water or the like containing hardness minerals is supplied as it is to the vessel, these minerals adhere to the membrane and the cathode with the lapse of long time to inhibit an electric current from flowing. There also is a possibility that the resultant deposit might cause clogging in the spray. It is preferred to dispose an ion-exchange resin or activated carbon in the tube or vessel for the purpose of preventing such troubles. This measure is unnecessary when the feed water is acid. It is also preferred to intermittently clean the vessel with an acid.

Spray Apparatus

The electrolytic water ejecting apparatus or electrolytic-water generator/spray apparatus of the invention preferably is one in which the electrolytic unit comprising electrodes and optionally including a diaphragm has been disposed in a transport tube disposed in the vessel for containing raw water. A head has been connected to the opening of the vessel, and a nozzle for ejecting or spraying the electrolytic water to be yielded has been disposed in the head.

The head may have a battery mounted therein. However, the apparatus may be equipped with a device which generates power for electrolysis upon operation of, e.g., a trigger, without employing a battery as a power source. Examples of the device include a motor which works while being engaged with the trigger. This motor is usually disposed in a trigger spray and is rotated by manual trigger operation to generate an energy. This energy is utilized for electrolysis.

In the case of battery driving, the battery may be a secondary battery, which is rechargeable. It is also possible to operate the apparatus with an adapter capable of supplying DC power from an AC power source.

The apparatus of the invention can further has means for indicating that electrolysis is being conducted. Examples of the means include an LED lamp which is made on during voltage application by trigger operation.

It is preferred that the vessel-side end of the transport tube be tapered or slender. The other end is connected to the head.

A check valve is preferably disposed in a lower part of the tube to thereby prevent the liquid present in the tube from flowing backward to dry the membrane in the tube. It is also preferred to make the lower part long and fold it to thereby prevent the backflow.

Although the apparatus of the invention desirably is of the trigger type, it may be of another type.

Figure 3:
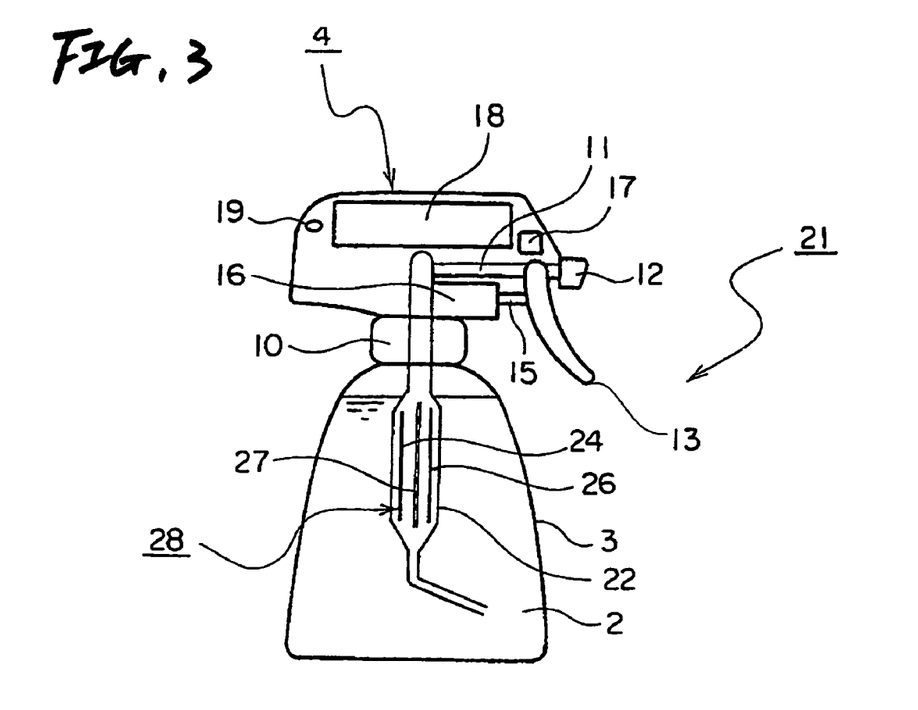
FIG. 3 is a schematic vertical sectional view illustrating a second embodiment of the electrolytic-water spray apparatus of the invention.
Figures 4A, 4B:
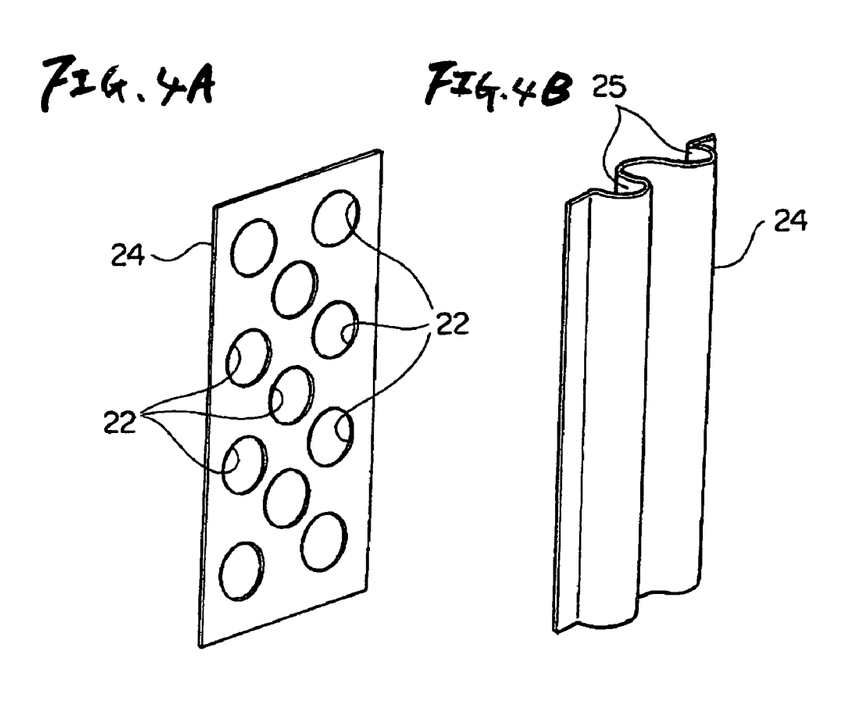
FIG. 4A is an enlarged view of the anode of the apparatus shown in FIG. 3.
FIG. 4B is an enlarged view showing another anode as an example.

This apparatus works by the following mechanism. The apparatus is switched on by, e.g., a trigger operation to cause a current to flow through the circuit. As a result, the current flows through the electrodes in the electrolytic unit to conduct electrolysis. The raw water present in the transport tube is almost instantaneously electrolyzed and converted to electrolytic water. This electrolytic water is discharged outward in an atomized or liquid state through the nozzle of the head by a piston/cylinder mechanism optionally with the aid of the power of, e.g., a pump. Namely, electrolysis is conducted simultaneously with the spraying (ejection) operation (e.g., trigger operation). It is preferred that electrolytic water yielded by electrolysis should begin to be sprayed (ejected) within 1 second after the initiation of the trigger operation.

The values of the voltage and current to be applied are suitably determined according to the concentration suitable for obtaining given sterilizing activity suitable for the substance to be sprayed (treated with the ejected electrolytic water) and for the purpose of spraying (ejection), e.g., deodorization or sterilization, and to the volume of the solution to be electrolyzed, etc. It is desirable that one trigger operation results in the spraying (ejection) of 0.1-1 cc of electrolytic water and in application of about 3-25 V between the electrodes. A device for changing the voltage to be applied to the electrodes may be disposed in the circuit as described above.

A switch for initiating/terminating voltage application to the electrodes may be disposed in the trigger spray so that a voltage is applied only when the apparatus is in use, i.e., pulling the trigger automatically results in switching on and returning the trigger results in switching off.

The ozone generator/spray apparatus of the invention as a spray apparatus equipped with a trigger spray can have various constitutions.

There are trigger sprays having various mechanisms. The trigger sprays differ in the liquid passage therein, the position of the fulcrum of the trigger, etc. according to the mechanisms thereof When a trigger is used in the invention, however, any desired trigger spray can be employed.

The following apparatus is one embodiment of the electrolytic-water generator/spray apparatus of the invention described above.

This apparatus comprises a vessel main body for containing raw water and a trigger spray (head) attached to the opening of the main body. The trigger spray comprises: a spray main body having a horizontal channel and a vertical channel connected thereto and further having a piston/cylinder mechanism for supplying a liquid to the horizontal channel and vertical channel; a trigger rotatably attached to the spray main body; a spin element attached in front of the horizontal channel; a nozzle member attached in front of the spin element; an intake (water intake member) attached to the vertical channel; and a tube attached to the intake. The spray main body and the intake have an outside-air introduction hole for introducing outside air into the vessel main body. The apparatus further has, disposed in the tube, an electrolytic unit having electrodes for electrolyzing the raw water. Upon each spraying operation, this apparatus sprays a solution containing electrolytically yielded products, such as ozone and peroxides.

The electrolytic water ejecting apparatus (electrolytic-water spray apparatus) of the invention is explained below by reference to the embodiments shown in the drawings.

FIG. 1 is a schematic vertical sectional view illustrating a first embodiment of the electrolytic-water spray apparatus of the invention. FIG. 2 is an enlarged view illustrating the diaphragm and electrodes of the apparatus shown in FIG. 1. FIG. 3 is a schematic vertical sectional view illustrating a second embodiment of the electrolytic-water spray apparatus of the invention. FIG. 4A is slant views illustrating electrodes for use in the apparatus shown in FIG. 3.

The electrolytic-water spray apparatus 1 shown in FIGS. 1 and 2 comprises a vessel 3 in which raw water 2 is contained and a head 4 connected to the upper opening of this vessel 3. The material of the vessel 3 may be a rigid one or a flexible one. It is, however, preferred that the vessel 3 be made of a rigid material such as any of various rigid resins, a metal, a glass, or a ceramic. The capacity of the vessel 3 is preferably about 100-1,000 mL, more preferably 200-500 mL. The raw water 2 may be pure water or may be one containing one or more electrolytes, e.g., sodium chloride, potassium chloride, and magnesium chloride, dissolved therein.

In the vessel 3 has been disposed a transport tube 5. The lower end of the transport tube 5 is located in and open to the raw water 2, while the upper end thereof has a reduced diameter and extends into the head of peace 4. An electrolytic unit 6 comprising an anode, a cathode, and a diaphragm has been housed in this transport tube 5. As shown in FIG. 2, this electrolytic unit 6 comprises: an anode 7 which is a metal rod on which a conductive-diamond has been deposited; a diaphragm 8 which is a strip-foam ion-exchange membrane wound around the anode 7; and a cathode 9 comprising a metal wire wound around the diaphragm 8. Although the diaphragm 8 in FIG. 2 has been wound around the anode 7 so that the gap between adjacent strip edges is not constant, it may be wound so as to result in a constant gap.

The small-diameter upper part of the transport tube 5 functions as a vertical channel 10, and the upper end thereof is connected to a horizontal channel 11 in the head 4.

At the other end of the horizontal channel 11 has been disposed a spray nozzle 12. A fulcrum 14 of a trigger arm 13 has been disposed on the slightly inner side of the spray nozzle 12 so that the trigger arm 13 is swingably movable around the fulcrum 14. The trigger arm 13 has been connected to a piston rod 15 extending inward so that the piston rod 15 travels in a cylinder 16 according to the movement of the trigger arm 13.

Numeral 17 denotes a trigger-engaged switch disposed so as to be in contact with the trigger arm 13; 18 denotes a power source battery disposed in the head 4; and 19 denotes an LED which in on only when electrolysis is proceeding.

The electrolytic-water spray apparatus 1 having such constitution is held in a hand and an inward force is applied to the trigger arm 13 with the forefinger and middle finger. As a result, the trigger arm 13 swingably moves around the fulcrum 14, whereby the trigger-engaged switch 17 becomes on and a voltage is applied to the electrolytic unit 6. Simultaneously therewith, the piston in the cylinder 16 moves to lead the raw water 2 present in the vessel 3 to the electrolytic unit 6 in the transport tube 5, where this raw water 2 is electrolyzed to yield electrolytic water. The anode 7 in this electrolytic unit 6 has a conductive diamond layer formed on the surface thereof. By the action of this conductive diamond, electrolytic water containing ozone or other active species dissolved therein in a high concentration is obtained.

The electrolytic water yielded instantaneously passes through the vertical channel 10 and horizontal channel 11 and is sprayed through the spray nozzle 12 on a substance to be sterilized.

The electrolytic-water spray apparatus shown in FIG. 3 is a modification of the apparatus shown in FIG. 1. Like members as in FIG. 1 are designated by like numerals, and explanations thereon are omitted. FIG. 4A is an enlarged view of the anode in FIG. 3, while FIG. 4B is an enlarged view of another anode.

The vessel 3 of this electrolytic-water spray apparatus 21 has a transport tube 22 disposed therein. The lower end of the tube 22 is tapered or slender and is located in an open to the raw water 2, while the upper end thereof has a reduced diameter and extends into the head 4. In this transport tube 22 has been disposed an electrolytic unit 28 comprising an anode 24 having many openings and a conductive diamond layer formed thereon, a cathode 26 of a flat plate shape, and a porous diaphragm 27 which separates the anode 24 and cathode 26 from each other.

In this electrolytic-water spray apparatus 21 also, when a force is applied to the trigger arm 13, the trigger-engaged switch 17 becomes on and a voltage is applied to the electrolytic unit 28. Simultaneously therewith, the raw water 2 present in the vessel 3 is led to the electrolytic unit 28 in the transport tube 22, where this raw water 2 is electrolyzed to yield electrolytic water. The electrolytic water yielded instantaneously passes through the vertical channel 10 and horizontal channel 11 and is sprayed through the spray nozzle 12 on a substance to be sterilized.

Incidentally, the anode 24 may be replaced by an anode 24' obtained by bending a flat plate to form grooves 25 therein.

EXAMPLES

Examples and Comparative Examples concerning the production of electrolytic water with electrolytic-water spray apparatus according to the invention and sterilization with electrolytic water is now illustrated below, but it should be understood that the present invention is not to be construed as being limited thereto.

Example 1

Figure 1:
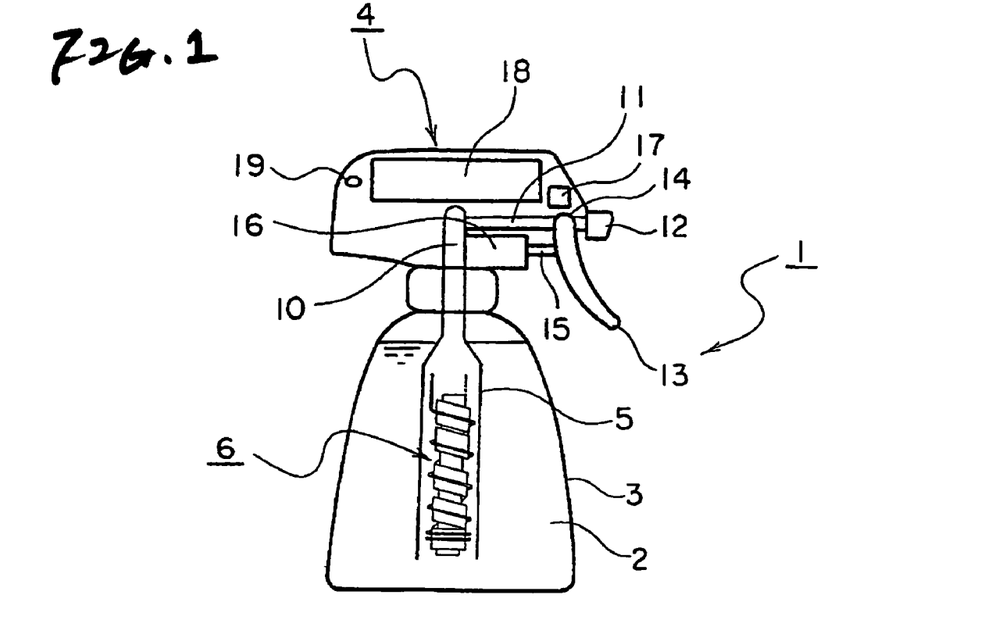
FIG. 1 is a schematic vertical sectional view illustrating a first embodiment of the electrolytic-water spray apparatus of the invention.
Figure 2:
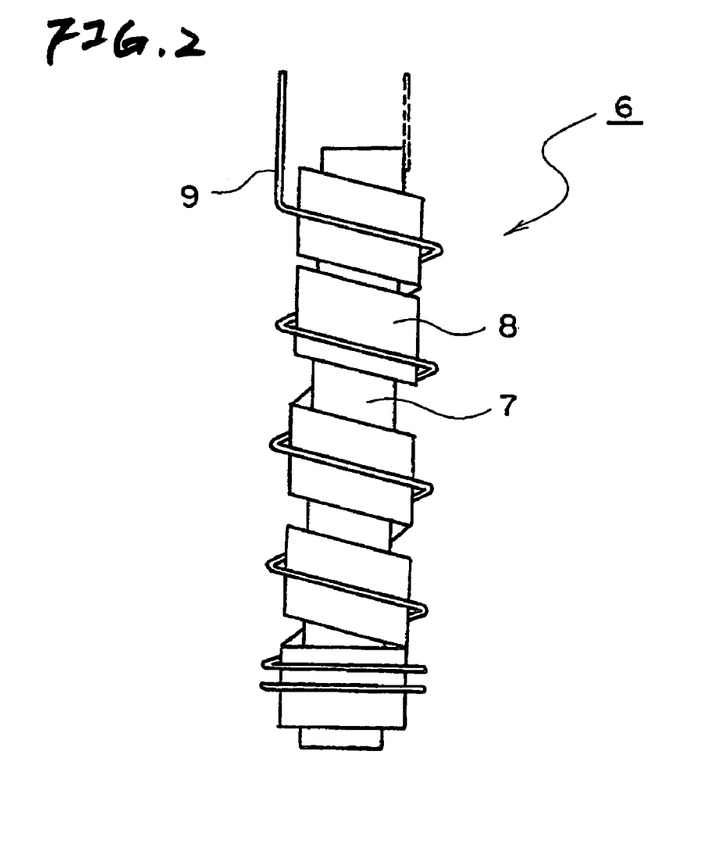
FIG. 2 is an enlarged view illustrating the diaphragm and electrodes of the apparatus shown in FIG. 1.

A rod made of niobium (diameter, 2 mm; length, 10 cm) on which a conductive-diamond had been deposited (thickness of the diamond, 3 μm; dopant boron concentration, 500 ppm) was used as an anode. A strip of an ion-exchange membrane (Nafion 350, manufactured by DuPont; thickness, 0.4 mm; width, 1 mm) was wound as a diaphragm around the anode. A commercial platinum wire (diameter, 0.5 mm) was wound as a cathode on the diaphragm to unite the anode, membrane, and cathode. This assembly (electrolytic unit; effective electrode area, 6 cm$^2$) was fixed to the inside of a transport PE resin tube in a trigger type spray apparatus as shown in FIGS. 1 and 2.

A 9V rectangular battery was mounted in the head of the trigger type spray apparatus. In a circuit part, the electrode terminals were connected to a variable resistor and a switch with a wiring. The vessel was filled with 500 cc of pure water. The trigger was pulled, upon which the circuit was switched on and a current flowed between the battery and the electrolytic unit. Simultaneously therewith, pure water (electrolytic water) was sprayed. The amount of the water sprayed was about 0.5 cc, and the quantity of electricity which flowed during this operation was 0.15 C (0.5 s×0.3 A). The terminal voltage of the electrolytic unit was 7 V The operation was repeatedly conducted 10 times. As a result, the ozone concentration in the electrolytic water sprayed, which amounted to about 5 cc, was 2.5 ppm (corresponding to a current efficiency of 10%). The trigger operation was repeated 2,000 times, and the concentration of the ozone-containing water measured thereafter also was 2.5 ppm. The operation could be conducted 2,400 times with the capacity of the one battery, which was 0.1 Ahr (360 C). The ozone-containing water was placed in a sealed glass vessel and stored at room temperature. As a result, the ozone concentration had decreased to 0.2 ppm or lower at 2 hours after the storage initiation.

In each of the Examples and Comparative Examples, the ozone concentration and hypochlorous acid concentration were determined with an ultraviolet spectrophotometer.

Example 2

The same test as in Example 1 was conducted, except that the vessel was filled with pure water containing 0.1 g/L acetic acid. As a result, the ozone concentration in the solution yielded was 3.5 ppm. The terminal voltage of the electrolytic unit was 7 V and the current was 0.3 A. The ozone-containing water was stored at room temperature in a sealed glass vessel. As a result, the initial concentration was maintained even after 2 hours. The trigger operation was repeated 2,000 times. As a result, the current efficiency in each operation was almost equal to the initial value.

Example 3

The same test as in Example 1 was conducted, except that the vessel was filled with tap water containing 2 g/L sodium chloride. As a result, the ozone concentration and hypochlorous acid concentration in the solution yielded were 0.8 ppm and 20 ppm, respectively. The terminal voltage of the electrolytic unit was 6.5 V and the current was 0.35 A. The trigger operation was repeated 2,000 times. As a result, the current efficiency in each operation was almost equal to the initial value, and a deposit of calcium and magnesium compounds was observed on the cathode of the electrolytic unit.

Example 4

The same test as in Example 1 was conducted, except that the vessel was filled with tap water containing 2 g/L sodium chloride and 0.1 g/L acetic acid. As a result, the ozone concentration and hypochlorous acid concentration in the solution yielded were 1 ppm and 20 ppm, respectively. The terminal voltage of the electrolytic unit was 6.5 V and the current was 0.35 A. The trigger operation was repeated 2,000 times. As a result, the current efficiency in each operation was almost equal to the initial value, and a deposit of calcium and magnesium compounds was not observed on the cathode of the electrolytic unit.

Example 5

The same test as in Example 1 was conducted, except that the vessel was filled with pure water containing 0.5 g/L sodium sulfate. As a result, the ozone concentration and persulfuric acid concentration in the solution yielded were 1.6 ppm and 20 ppm, respectively. The persulfuric acid was determined by reacting it with titanium sulfate under acid conditions and examining the resultant colored solution for absorbance. The terminal voltage of the electrolytic unit was 6 V and the current was 0.4 A. The trigger operation was repeated 2,000 times. As a result, the current efficiency in each operation was almost equal to the initial value.

Example 6

The same test as in Example 1 was conducted, except that the vessel was filled with pure water containing 0.5 g/L sodium carbonate. As a result, the ozone concentration and percarbonic acid concentration in the solution yielded were 1.6 ppm and 15 ppm, respectively. The percarbonic acid was determined by reacting it with titanium sulfate under acid conditions and examining the resultant colored solution for absorbance. The terminal voltage of the electrolytic unit was 6 V and the current was 0.4 A. The trigger operation was repeated 2,000 times. As a result, the current efficiency in each operation was almost equal to the initial value.

Example 7

The same test as in Example 1 was conducted, except that succinic acid and lauryldimethylamine oxide [Anhitol 20N, manufactured by Kao Corp.] as a surfactant were added to the vessel each in an amount of 50 ppm. The terminal voltage of the electrolytic unit was 7 V and the current was 0.3 A. The ozone concentration in the solution yielded was 3 ppm. The trigger operation was repeated 2,000 times. As a result, the current efficiency in each operation was almost equal to the initial value.

Comparative Example 1

Pure water was used as a feed material to conduct the same test as in Example 1, except that a rod made of titanium on which an iridium oxide (5 g/m$^2$) catalyst had been deposited was used as an anode. As a result, the terminal voltage of the electrolytic unit was 6 V and the current was 0.4 A. The ozone concentration in the solution was 0.1 ppm or lower, which was far lower than in the Examples.

Comparative Example 2

The same test as in Example 3 was conducted, except that a rod made of titanium on which an iridium oxide (5 g/m$^2$) catalyst had been deposited was used as an anode and tap water containing 0.1 g/L sodium chloride was used as raw water. As a result, the terminal voltage of the electrolytic unit was 5.5 V and the current was 0.45 A. The hypochlorous acid concentration and ozone concentration in the solution yielded were 24 ppm and 0.1 ppm or lower, respectively. The ozone concentration was far lower than in the Example, although the efficiency of hypochlorous acid generation was higher.

Comparative Example 3

The same test as in Example 1 was conducted, except that a rod made of titanium on which a platinum (20 g/m$^2$) catalyst had been deposited was used as an anode. As a result, the terminal voltage of the electrolytic unit was 6 V and the current was 0.4 A. The ozone concentration in the solution was 0.8 ppm. The trigger operation was repeated 2,000 times and, as a result, the ozone concentration decreased to 0.4 ppm. The ozone concentration was far lower than in the Example and the stability thereof was poor.

Comparative Example 4

The same test as in Example 3 was conducted, except that a rod made of titanium on which a platinum (20 g/m$^2$) catalyst had been deposited was used as an anode and tap water containing 0.1 g/L sodium chloride was used as raw water. As a result, the terminal voltage of the electrolytic unit was 5.5 V and the current was 0.45 A. The hypochlorous acid concentration and ozone concentration in the solution yielded were 3 ppm and 1 ppm, respectively. The trigger operation was repeated 2,000 times and, as a result, the ozone concentration decreased to 0.4 ppm. The efficiency of hypochlorous acid generation and ozone concentration were lower than in the Example.

Comparative Example 5

Electrolysis was conducted in the same manner as in Example 5, except that a rod made of titanium on which a platinum (20 g/m$^2$) catalyst had been deposited was used as an anode. As a result, the terminal voltage of the electrolytic unit was 5.5 V and the current was 0.45 A. The ozone concentration and persulfate ion concentration in the solution yielded were 0.8 ppm and 1 ppm or lower, respectively. The ozone concentration and the persulfuric acid concentration were lower than in the Example. The trigger operation was repeated 2,000 times and, as a result, the ozone concentration decreased to 0.4 ppm.

Comparative Example 6

Electrolysis was conducted in the same manner as in Example 6, except that a rod made of titanium on which a platinum (20 g/m$^2$) catalyst had been deposited was used as an anode. As a result, the terminal voltage of the electrolytic unit was 5.5 V and the current was 0.45 A. The ozone concentration and percarbonic acid concentration in the solution yielded were 0.6 ppm and 2 ppm, respectively. The ozone concentration and the percarbonic acid concentration were lower than in the Example. The trigger operation was repeated 2,000 times and, as a result, the ozone concentration decreased to 0.3 ppm.

Example 8

A rod made of titanium (diameter, 3 mm; length, 10 cm) was used as an anode base. A conductive-diamond (thickness of the diamond, 3 μm; dopant boron concentration, 1,300 ppm) was deposited on the substrate to obtain an anode. A strip of a hydrophilic diaphragm (Poreflon, manufactured by Sumitomo Electric Industries, Ltd.; thickness, 0.2 mm; width, 1 mm) was wound as a diaphragm around the anode. A stainless-steel wire (diameter, 0.5 mm) was wound as a cathode on the diaphragm. In the same manner as in Example 1, this assembly was fixed to the inside of a transport PE resin tube in a trigger type spray apparatus. The vessel was filled with tap water containing 0.5 g/L sodium chloride. The trigger was pulled to conduct electrolysis. During this electrolysis, the terminal voltage of the electrolytic unit was 5 V and the current was 0.5 A. The concentration of hypochlorous acid was 40 ppm. The trigger operation was repeated 2,000 times. As a result, the current efficiency remained almost equal to the initial value. A deposit of calcium and magnesium compounds was observed on the cathode of the electrolytic unit.

Example 9

A conductive-silicon plate anode having a length of 10 cm, width of 5 mm, and thickness of 1 mm and coated with conductive diamond having a thickness of 3 μm was used together with a cathode which was a stainless-steel plate having the same dimensions as the anode. An ion-exchange resin member having porosity was interposed as a diaphragm between the electrodes. This assembly was disposed in the transport tube in a trigger spray apparatus in the same manner as in Example 1. The electrode spacing was regulated to 1 mm. Pure water was used as raw water. A spraying operation was repeated 50 times under the same conditions as in Example 1, except that the spray amount was changed to about 0.1 cc. The ozone concentration in the solution sprayed, which amounted to about 5 cc, was 10 ppm.

Sterilization Test

*E. coli* (IFO03972) or *Bacillus cereus* (IFO13494) was used as a test microorganism. The microorganism was treated by an ordinary method and then subjected to a test. With respect to *E. coli*, one platinum earpick amount was taken therefrom after the pre-incubation, inoculated into an SCD culture medium (manufactured by Nihon Pharmaceutical Co., Ltd.), and incubated with shaking at 37° C. for 24 hours. Thereafter, the cells incubated were recovered by centrifugal separation and regulated so as to have a concentration of $10^7$ cells/mL in preparation for use in the test. On the other hand, with respect to *Bacillus cereus*, one platinum earpick amount was taken from the microorganism which had been pre-incubated in an SCD agar medium (manufactured by Nihon Pharmaceutical Co., Ltd.), suspended in 1 mL of sterilized water, heat-treated at 65° C. for 30 minutes, and then subjected twice to centrifugal separation/washing to prepare a cell suspension to be subjected to the test. This spore cell suspension for use in the test was regulated so as to have a concentration of $10^7$ cells/mL.

With respect to each of the two cell suspensions, 0.1 mL portions were taken therefrom and applied on stainless-steel plates (SUS304) having dimensions of 50 mm×50 mm. Using the spray apparatus of Example 1, the electrolytic waters obtained in Examples 1 to 7 and Comparative Examples 1 to 6 were sprayed on the stainless-steel plates. After the plate surfaces each were kept in contact with the water for 5 minutes or 1 minute in the case of *Bacillus cereus* or *E. coli*, respectively, they were wiped with a sterilized cotton swab. This cotton swab was immersed in an SCD LP medium (manufactured by Nihon Pharmaceutical Co., Ltd.) to which 3.3% aqueous sodium thiosulfate solution had been added, and the adherent substances were sufficiently dispersed in the medium. This medium was held at 37° C. for 48 hours for incubation and then examined for bacterial growth. Sterilizing activity was evaluated based on the following criteria.

A: completely sterilized (no bacterial growth was observed at all)

B: sterilization was incomplete (bacterial growth was observed)

The ozone concentrations of the electrolytic waters obtained in Examples 1 to 7 and Comparative Examples 1 to 6 and the results of the sterilization test are summarized in Table 1.

TABLE 1

| | Ozone concentration (ppm) | Results | Remarks |
|---|---|---|---|
| Example 1 | 2.5 | A | pure water only |
| Example 2 | 3.5 | A | acidified with acetic acid |
| Example 3 | 0.8 | A | hypochlorous acid, 20 ppm |
| Example 4 | 1 | A | acidified with acetic acid + hypochlorous acid, 20 ppm |
| Example 5 | 1.6 | A | persulfuric acid, 20 ppm |
| Example 6 | 1.6 | A | percarbonic acid, 15 ppm |
| Example 7 | 3 | A | with additives |
| Comparative Example 1 | <0.1 | B | pure water only |
| Comparative Example 2 | <0.1 | A | hypochlorous acid, 24 ppm |
| Comparative Example 3 | 0.6 (average) | B | pure water only |
| Comparative Example 4 | 0.7 (average) | B | hypochlorous acid, 3 ppm |
| Comparative Example 5 | 0.5 (average) | B | persulfuric acid, $\leq$1 ppm |
| Comparative Example 6 | 0.45 (average) | B | persulfuric acid, 2 ppm |

While the present invention has been described in detail and with reference to specific embodiments thereof, it will be apparent to one skilled in the art that various changes and modifications can be made therein without departing from the spirit and scope thereof.

The present application is based on Japanese Patent Application No. 2005-176801 filed on Jun. 16, 2005, and the contents thereof are incorporated herein by reference.

What is claimed is:

1. An electrolytic water ejecting apparatus comprising:
   a vessel containing a raw water;
   an electrolytic unit comprising: a cathode; and an anode at least having a part containing a conductive diamond;
   a head to eject an electrolytic water prepared by electrolyzing the raw water with the electrolytic unit, and
   a sheet-form diaphragm member;
   wherein the anode has a shape of a rod and the cathode has a shape of a wire, and the sheet-form diaphragm member is disposed around the anode and the cathode is disposed around the sheet-form diaphragm member, and
   wherein the sheet-form diaphragm member is spirally wound around the rod anode so that gaps are present between adjacent strip edges of the spirally wound sheet-form diaphragm member.

2. The electrolytic water ejecting apparatus of claim 1, wherein the width of the gaps between adjacent strip edges is between 1-10 mm.

3. The electrolytic water ejecting apparatus of claim 1, wherein the sheet-form diaphragm member is in contact with the rod anode.

* * * * *